United States Patent [19]

Blum et al.

[11] 4,410,752

[45] Oct. 18, 1983

[54] PROCESS FOR THE OXYDEHYDROGENATION OF ETHANE TO ETHYLENE

[75] Inventors: Patricia R. Blum, Macedonia; Ernest C. Milberger, Solon, both of Ohio

[73] Assignee: The Standard Oil Company, Cleveland, Ohio

[21] Appl. No.: 346,029

[22] Filed: Feb. 5, 1982

Related U.S. Application Data

[63] Continuation-in-part of Ser. No. 168,240, Jul. 10, 1980, abandoned.

[51] Int. Cl.³ .......................... C07C 5/38; C07C 5/48
[52] U.S. Cl. .................................. 585/658; 585/660; 585/663; 502/209; 502/304
[58] Field of Search ............... 585/658, 661, 662, 663, 585/660; 252/437

[56] References Cited

U.S. PATENT DOCUMENTS 3,851,881 12/1974 Manning .............................. 585/658
4,172,084 10/1979 Bremer ................................ 252/437

Primary Examiner—Delbert E. Gantz
Assistant Examiner—A. Pal
Attorney, Agent, or Firm—Joseph G. Curatolo; Herbert D. Knudsen; Larry W. Evans

[57] ABSTRACT

The invention herein is directed toward a process for the oxydehydrogenation of ethane in fixed-bed or fluid-bed reactors at temperatures of less than about 600° C. The process includes the step of contacting ethane and an oxygen-containing gas with a catalyst composition having the formula $V_{1.0}P_aO_x$. The catalyst can be employed in supported or unsupported form. A promoter metal can optionally be present in the catalyst.

12 Claims, No Drawings

PROCESS FOR THE OXYDEHYDROGENATION OF ETHANE TO ETHYLENE

CROSS REFERENCE TO RELATED APPLICATIONS

This application is a continuation-in-part of U.S. Ser. No. 168,240, filed July 10, 1980 now abandoned.

TECHNICAL FIELD

The catalytic oxidative dehydrogenation of hydrocarbons has recently become of major industrial importance. While highly selective processes for the oxidation of monoolefins have been developed, the selective oxidation of paraffins has been less successful. The present invention provides a process for the preparation of ethylene from ethane by oxydehydrogenation. Ethylene is prepared from ethane in the presence of oxygen and a catalyst having the formula $V_{1.0}P_aO_x$, where a is 0.5 to 3.0 and x is equal to that value which satisfies the valence requirements. The catalyst can optionally contain a promoter metal $M_b$, where b is 0.0. to 1.0.

BACKGROUND ART

Ethylene is commercially prepared by thermally cracking ethane at temperatures of 600° to 1000° C. The reaction, being endothermic, is costly due to high energy input and because the reaction vessels require special materials. At such temperatures, the reaction time is very short making the efficient recovery of heat from the process stream difficult. And, production of by-products adds to the difficulty and expense of ethylene recovery.

A process for the oxidative dehydrogenation of olefins is set forth in U.S. Pat. No. 3,856,881. This patent employs a catalyst containing vanadium, oxygen and at least one other metallic element. The patent states that a face-centered cubic form of crystalline structure is preferred and exemplifies the disclosure with vanadites of spinel structure. Phosphorus, is an optional element and, when present, the patent states that it should be in an amount of from about 0.002 to 0.35 atom of phosphorus per atom of vanadium, and preferably between about 0.005 and 0.20 atoms of phosphorus per atom of vanadium.

The patent states that the vanadium spinel compositions exhibit a certain type of X-ray diffraction pattern, one which does not have any sharp X-ray diffraction reflection peaks typical of a highly crystalline material having the same chemical structure. While this is true for vanadium spinel compositions, we have found such structures poorly suited for the oxydehydrogenation of ethane.

Ethane can be oxydehydrogenated to form ethylene with various oxyhalogenation catalyst systems at temperatures of 500° to 600° C. However, the presence of the halogen increases the recovery cost of the ethylene and requires special materials that withstand corrosion for construction of the reactors.

One process is known, however, for the oxydehydrogenation of ethane to ethylene at relatively low temperatures, which does not require special reactor materials and which provides relatively high levels of conversion, selectivity and productivity. This process involves the use of catalysts comprising mixed oxides of molybdenum and vanadium, together with a transition metal oxide; one optimum catalyst has the composition $Mo_{0.61}V_{0.31}Nb_{0.08}O_x$. Preparation and use of this catalyst is discussed in U.K. Pat. No. 1,538,107 as well as a paper from Union Carbide, E. M. Thornsteinson, T. P. Wilson, F. G. Young and P. H. Kasai, *J. of Catalysis*, 52, 116-132 (1978). The authors reported a selectivity to ethylene of 83% at 25% conversion of ethane under atmospheric pressure and at 340° C.

While the oxidation of paraffins is difficult, those having at least four carbon atoms are more reactive to catalytic conversion than is ethane. Butane, which is far less refractory than ethane, is converted to maleic anhydride in the presence of certain vanadium-phosphorus catalysts with various promoter elements. These catalysts are described in several U.S. patents of which we are aware, viz., U.S. Pat. Nos. 4,002,650 and 4,172,084, commonly owned by the Assignee of record herein, and U.S. Pat. No. 4,043,943. Notwithstanding the use of these catalysts for conversion of butane, we are unaware of their use as a catalyst for the oxydehydrogenation of ethane.

DISCLOSURE OF THE INVENTION

It is therefore an object of the present invention to provide a process for the oxydehydrogenation of ethane to ethylene which does not utilize extremely high temperatures or result in corrosion of the reaction vessel.

It is another object of the present invention to provide a process for the oxydehydrogenation of ethane to ethylene which is relatively highly selective for ethylene formation and which provides good total conversions to ethylene with minimal carbon-oxygen by-products such as acetic acid, carbon monoxide and carbon dioxide.

It is yet another object of the present invention to provide a process for the oxydehydrogenation of ethane to ethylene utilizing a catalyst comprising the mixed oxides of vanadium and phosphorus.

It is still another object of the present invention to provide a process for the oxydehydrogenation of ethane to ethylene utilizing a catalyst that can optionally contain a promoter metal.

These and other objects, together with the advantages thereof over the prior art, which shall become apparent from the specification which follows are accomplished by our invention as hereinafter described and claimed.

In general, the process of the present invention includes the step of contacting ethane and an oxygen containing gas at a temperature of at least 300° C. with a catalyst composition having the formula $V_{1.0}P_aO_x$. The step of contacting includes the step of feeding ethane with an oxygen-containing gas to either a fixed-bed or fluid-bed reactor containing the catalyst which can be supported or unsupported. The catalyst can optionally contain a promoter metal.

PREFERRED MODE FOR CARRYING OUT THE INVENTION

The catalyst employed in the practice of our invention has the formula $V_{1.0}P_aM_bO_x$ wherein M is a promoter element such as Co, Cu, Fe, Ni, Nb, Mo, Cr, W, U, Ta, Ti, Zr, Zn, Hf, Mn, Pt, Pd, Sn, Sb, Bi, Ce, As, Ag or Au including combinations thereof; a is 0.5 to 3.0 and preferably 0.85 to 2.0; b is 0.0 to 1.0 and preferably 0.0 to 0.4 and x is that value which satisfies the valence requirements of the other elements.

Preparation of these catalysts is substantially the same as the preparation of catalysts which effect the conversion of butane to maleic anhydride. Typical preparations have been set forth in U.S. Pat. Nos. 4,002,650, 4,043,943 and 4,172,084 mentioned hereinabove, the subject matter of which is hereby incorporated by reference.

If desired the catalyst may be used unsupported or supported. When supported on substances such as aluminum oxide, silicon carbide, zirconia, titania, Alundum or mixtures thereof, the catalyst comprises about 10 to 80 percent by weight of the total weight.

The oxydehydrogenation reaction is conducted in a fixed-bed reactor at a temperature ranging from about 300° to about 600° C. Pressure is preferably atmospheric although pressures of from about 0.5 to about 3 atmospheres can be employed. The catalyst can be utilized in any of the conventional fixed-bed forms such as tablet, pellet, extruded and spherical.

The hydrocarbon feed, ethane, is fed to the reactor in a stream of air or oxygen in an inert gas such as nitrogen wherein the oxygen content comprises at least 10 percent by volume of the carrier gas and the ratio of air to hydrocarbon is about 2.5:1 to about 30:1, again on a volume basis. Contact time of the hydrocarbon with the catalyst can range from 0.5 to 10 seconds or more at reactor conditions with about one to five seconds being usual.

Ethane conversion to ethylene was conducted with several different catalyst compositions reported hereinbelow. The work was conducted in a stainless steel microreactor having a 20 cc volume. The reactor space was filled with the catalyst and ethane with air was fed therethrough. The effluent comprising ethylene, ethane and by-products was analyzed to determine the percent selectivity to ethylene, which is defined as follows:

$$\text{Yield } C_2H_4 = \frac{\text{Moles of ethylene recovered}}{\text{Moles of ethane fed}} \times 100$$

$$\text{Total Conversion} = \frac{\text{Moles ethane fed} - \text{Moles ethane recovered}}{\text{Moles ethane fed}} \times 100$$

$$\text{Percent Selectivity} = \frac{\text{Moles of ethylene recovered}}{\text{Moles of ethane reacted}} \times 100$$

The examples which follow are intended only to be exemplary and should not be construed as limiting this invention in any way. Numbers 1 to 4 were conducted with the catalyst $V_{1.0}P_{1.0}O_x$ prepared in isobutanol with no additional reducing agent. Numbers 5–7 were conducted with the catalyst $V_{1.0}P_{1.0}O_x$ prepared in water and reduced with hydrazine. Numbers 8 to 13 were conducted with the catalyst $V_{1.0}P_{1.15}U_{0.2}O_x$ prepared in water and concentrated aqueous hydrochloric acid; numbers 14 to 17 were conducted with the catalyst $V_{1.0}P_{1.15}U_{0.2}W_{0.05}+W_{0.166}$° prepared in water and reduced with tungsten; numbers 18 to 20 conducted with the catalyst $V_{1.0}P_{1.15}W_{0.2}O_x$ prepared in water and reduced with hydrazine; numbers 21 to 24 were conducted with the catalyst $V_{1.0}P_{1.14}Co_{0.19}O_x$ prepared in isobutanol with anhydrous hydrogen chloride; and numbers 25 to 29 were conducted with the catalyst $V_{1.0}P_{1.14}U_{0.2}O_x$ also prepared in isobutanol with anhydrous hydrogen chloride.

The vanadyl phosphate catalyst employed for practice of the process of the present invention, including those catalysts exemplified and described above, has a discrete and unique structure and can be characterized by its X-ray diffraction (XRD) pattern which is as follows:

| d(Å) | I |
| --- | --- |
| 6.3 | 10 |
| 4.8 | 7 |
| 3.9 | 100 |
| 3.13 | 58 |
| 2.93 | 29 |
| 2.65 | 7 |

Generally to obtain this crystalline structure, a catalyst may be prepared according to U.S. Pat. No. 4,172,084 as stated hereinabove. In addition to the components and conditions set forth in the patent, other solvents and reducing agents can be employed and the reaction temperatures and pressures can be varied. After the catalyst precursor is obtained, it is then activated by calcining. During calcining, the crystalline structure specified hereinabove is formed which is the structure used in the process of the present invention. Depending upon the mode of preparation, a greater or lesser amount of the crystalline phase may be formed. But in any event, this crystalline structure must be present for the catalyst to be suitable for the process of the present invention.

The catalyst can be promoted with one or more of the promoter metals disclosed herein without affecting the foregoing XRD pattern. Catalysts having the chemical composition of those catalysts disclosed herein but which do not have the identical crystalline phase can readily be converted thereto by reduction or heating in air or a reducing gas, depending upon the process employed for preparation of the catalyst. For purposes of the present invention, the preparation of the catalyst does not constitute any part thereof. However, it is necessary that the catalyst have the formula set forth having vanadium and phosphorus, the latter element being present in an amount of at least 0.5 and preferably at least 0.85 atom per atom of vanadium. The catalyst must also contain the crystalline structure that is characterized by the XRD pattern presented hereinabove.

Regarding the use of promoter metals, we have found that while the vanadium, phosphorus, oxygen catalyst performed well for the oxydehydrogenation of ethane, the addition of one or more promoter metals does not weaken or destroy the activity of the catalyst by changing its crystalline structure, but rather the crystalline structure desired is maintained. The utility of the promoter elements is that their presence often allows for an easing of reaction conditions such as permitting lower reaction temperatures, shorter contact times and the like.

TABLE I

Oxydehydrogenation of Ethane with Various Catalysts

| Example No. | Temp. °C. | Air/ HC[a] | WWH[b] | C.T. sec.[c] | Yield $C_2H_4$ % | % Sel for $C_2H_4$ | Total Conversion |
| --- | --- | --- | --- | --- | --- | --- | --- |
| 1 | 388 | 7 | 0.050 | 6 | 15.20 | 59.5 | 25.6 |
| 2 | 407 | 6 | 0.050 | 6 | 17.60 | 54.8 | 32.1 |
| 3 | 428 | 6 | 0.050 | 6 | 18.40 | 59.2 | 31.0 |
| 4 | 450 | 7 | 0.050 | 6 | 18.40 | 56.9 | 32.4 |
| 5 | 426 | 8 | 0.044 | 6 | 9.67 | 59.41 | 16.27 |
| 6 | 457 | 8 | 0.044 | 6 | 17.54 | 41.66 | 42.10 |
| 7 | 484 | 8 | 0.044 | 6 | 17.47 | 32.07 | 54.48 |
| 8 | 395 | 13 | 0.045 | 4 | 4.13 | 76.58 | 5.39 |
| 9 | 436 | 14 | 0.044 | 4 | 9.90 | 72.33 | 13.69 |
| 10 | 489 | 14 | 0.044 | 3 | 19.01 | 55.36 | 34.21 |
| 11 | 516 | 13 | 0.044 | 4 | 22.67 | 43.16 | 52.53 |

TABLE I-continued
Oxydehydrogenation of Ethane with Various Catalysts

| Example No. | Temp. °C. | Air/ HC[a] | WWH[b] | C.T. sec.[c] | Yield C₂H₄ % | % Sel for C₂H₄ | Total Conversion |
|---|---|---|---|---|---|---|---|
| 12 | 437 | 13 | 0.048 | 3 | 13.23 | 69.30 | 19.09 |
| 13 | 475 | 14 | 0.047 | 3 | 19.32 | 54.85 | 35.22 |
| 14 | 407 | 14 | 0.055 | 4 | 4.57 | 66.97 | 6.83 |
| 15 | 454 | 14 | 0.055 | 4 | 9.03 | 62.30 | 14.49 |
| 16 | 486 | 14 | 0.054 | 4 | 12.55 | 50.08 | 25.07 |
| 17 | 520 | 14 | 0.054 | 3 | 16.47 | 34.09 | 48.32 |
| 18 | 422 | 13 | 0.045 | 4 | 4.73 | 50.21 | 9.42 |
| 19 | 467 | 13 | 0.046 | 3 | 7.54 | 32.20 | 23.41 |
| 20 | 511 | 13 | 0.047 | 3 | 11.08 | 21.26 | 52.13 |
| 21 | 345 | 13 | 0.042 | 4 | 9.41 | 47.73 | 19.71 |
| 22 | 345 | 13 | 0.042 | 4 | 9.65 | 49.73 | 19.40 |
| 23 | 381 | 13 | 0.042 | 4 | 9.42 | 32.25 | 37.05 |
| 24 | 407 | 13 | 0.041 | 4 | 9.21 | 27.43 | 54.10 |
| 25 | 404 | 8 | 0.070 | 4 | 11.93 | 49.20 | 31.89 |
| 26 | 406 | 10 | 0.049 | 4 | 17.51 | 40.39 | 42.24 |
| 27 | 406 | 10 | 0.051 | 4 | 19.37 | 41.23 | 47.07 |
| 28 | 404 | 10 | 0.051 | 4 | 18.01 | 37.18 | 48.50 |
| 29 | 415 | 10 | 0.051 | 4 | 20.50 | 36.26 | 56.61 |

[a] Air/hydrocarbon ratio on volume basis
[b] Weight of hydrocarbon/(weight of catalyst) × (hour)
[c] Contact time at reactor conditions As can be seen from the data presented in Table I, total conversion to ethylene was generally greater than 10 percent, depending upon the temperature in the reactor bed, and percent selectivity for ethylene was generally greater than 50 percent. Although the catalyst performed quite well with no promoter metals present, it can be seen that the presence of a promoter was beneficial to the activity, because the basic crystalline structure of the catalyst represented by the above-noted XRD pattern was not affected. Of the examples reported, the highest yield of ethane to ethylene was 22.67 percent (Example No. 11). This should not be considered the optimum yield of ethylene to be obtained by this process, on the contrary, a judicious choice of promoter(s), mode of preparation, mode of reactor operation and process conditions would very likely result in significantly higher yields of ethylene.

Based upon the oxydehydrogenation of ethane reported herein it should be apparent that the objects of the invention have been met. As stated hereinabove, the catalysts that can be employed in the practice of the process of this invention can contain one or more of the promoter elements disclosed herein. It is therefore to be understood that variations of the disclosure fall within the scope of the claimed invention and that the subject invention is not to be limited by the examples set forth herein. They have been provided merely to demonstrate operability and therefore the selection of other catalyst components can be determined without departing from the spirit of the invention herein disclosed and described. Moreover, the scope of the invention shall include all modifications and variations that fall within the scope of the attached claims.

We claim:

1. A process for the oxydehydrogenation of ethane comprising the step of:
contacting ethane and an oxygen-containing gas at a temperature of at least 300° C. with a catalyst composition having the formula $V_{1.0}P_aM_bO_x$ wherein M is a promoter element selected from the group consisting of Co, Cu, Fe, Ni, Nb, Mo, Cr, W, U, Ta, Ti, Zr, Zn, Hf, Mn, Pt, Pd, Sn, Sb, Bi, Ce, As, Ag and Au; a is 0.5 to 3.0; b is 0.0 to 1.0 and x is the value which satisfies the valence requirements of all the elements, said catalyst having a crystalline structure represented substantially by the X-ray diffraction pattern

| d(Å) | I |
|---|---|
| 6.3 | Weak |
| 4.8 | Weak |
| 3.9 | Strong |
| 3.13 | Strong |
| 2.93 | Moderate |
| 2.65 | Weak. |

2. A process, as set forth in claim 1, wherein said step of contacting ethane is conducted in a fixed bed reactor at a temperature of from about 300° C. to about 600° C.

3. A process, as set forth in claim 1, wherein said oxygen-containing gas is selected from the group consisting of air, oxygen in air and oxygen in nitrogen.

4. A process, as set forth in claim 3, wherein the ratio of air to ethane is from about 2.5:1 to about 30:1 by volume.

5. A process, as set forth in claim 1, wherein the promoter element is selected from the group consisting of Co, U and W.

6. A process, as set forth in claims 1 or 5, wherein a is 0.85 to 2.0 and b is 0.0 to 0.4.

7. A process, as set forth in claim 6, wherein the crystalline structure of said catalyst is represented substantially by the X-ray diffraction pattern

| d(A) | I |
|---|---|
| 6.3 | 10 |
| 4.8 | 7 |
| 3.9 | 100 |
| 3.13 | 58 |
| 2.93 | 29 |
| 2.65 | 7 |

8. A process, as set forth in claim 6, wherein the composition of said catalyst is $V_{1.0}P_{1.0}O_x$.

9. A process, as set forth in claim 6, wherein the composition of said catalyst is $V_{1.0}P_{1.15}U_{0.2}O_x$.

10. A process, as set forth in claim 6, wherein the composition of said catalyst is $V_{1.0}P_{1.15}U_{0.2}W_{0.05}+W_{0.166}$°.

11. A process, as set forth in claim 6, wherein the composition of said catalyst is $V_{1.0}P_{1.15}W_{0.2}O_x$.

12. A process, as set forth in claim 6, wherein the composition of said catalyst is $V_{1.0}P_{1.14}Co_{0.19}O_x$.

* * * * *